(12) United States Patent
Manning

(10) Patent No.: US 7,128,393 B2
(45) Date of Patent: Oct. 31, 2006

(54) HIGHLY PARALLEL FABRICATION OF MICROARRAYS BY INK JET PRINTHEADS

(75) Inventor: Howard John Manning, Edinburgh (GB)

(73) Assignee: Array Jet Limited, Edinburgh (GB)

(*) Notice: Subject to any disclaimer, the term of this patent is extended or adjusted under 35 U.S.C. 154(b) by 578 days.

(21) Appl. No.: 10/350,776

(22) Filed: Jan. 24, 2003

(65) Prior Publication Data
US 2004/0145631 A1 Jul. 29, 2004

(51) Int. Cl.
*B41J 2/21* (2006.01)
(52) U.S. Cl. .......................... 347/43; 347/56
(58) Field of Classification Search .................. 347/20, 347/15, 43, 61–65, 67, 56, 22, 24, 28
See application file for complete search history.

(56) References Cited

U.S. PATENT DOCUMENTS 5,367,324 A * 11/1994 Abe et al. ..................... 347/43
5,658,802 A 8/1997 Hayes et al.
6,083,763 A 7/2000 Balch

FOREIGN PATENT DOCUMENTS

WO  WO 98/45205   10/1998
WO  WO 00/51736   9/2000

* cited by examiner

Primary Examiner—Juanita D. Stephens
(74) Attorney, Agent, or Firm—Workman Nydegger

(57) ABSTRACT

A method is described of operating an ink jet printhead having one or more manifolds each connected to more than one chamber, each chamber being associated with a nozzle and capable of ejecting drops therefrom: a number of different liquids larger than the number of manifolds is introduced into the printhead via the nozzles; and the volume of the liquid subsequently printed from each nozzle is less than the volume of the chamber associated with that nozzle, and also less than the volume of liquid introduced into that chamber. By this means the printhead prints more different liquids than is conventionally possible without mixing them.

26 Claims, 1 Drawing Sheet

HIGHLY PARALLEL FABRICATION OF MICROARRAYS BY INK JET PRINTHEADS

CROSS-REFERENCE TO RELATED APPLICATIONS

This application claims priority to PCT Application No. PCT/GB01/03471, filed Aug. 2, 2001, which applications is incorporated herein by specific reference.

BACKGROUND OF THE INVENTION

1. The Field of the Invention

This filed to the use of ink jet printers to make biological microarrays.

2. The Relevant Technology

Advances in biological and chemical science are demanding the testing of large numbers of samples in parallel. For example, the sequencing of human and animal genomes has created a need to determine the function of genes through expression studies. In this field, in pharmacogenomics and toxicology screening, and in many other applications, there is a need to test a large number of interactions between probe and target.

A technology which has emerged to address this need is the microarray, also known as the DNA microarray or biochip, and by other terminology. This consists of a substrate on which a compact array of biological or chemical samples, known as probes, is immobilised. The microarray is exposed to a sample, known as the target, which is to be tested against the probes. The interactions are recorded by suitable instrumentation and the data is manipulated.

Microarrays are made at present by two methods: the probes can be synthesised on the array, by applying constituents of the probes to build them up in situ; or pre-synthesised probes can be spotted onto the array. This invention relates to the latter method.

The task of spotting a microarray consists of transferring extremely small amounts of many different liquids from separate reservoirs to closely spaced positions on a number of microarrays. There may be anything from tens of different liquids to hundreds of thousands of them, supplied typically in multiple 96, 384 or 1536-well microtitre plates. Some tens or hundreds of substrates need to be spotted with each of the liquids; typical spot volumes are of the order of a nanolitre, and spots may be separated by a few hundred microns.

Spotting is achieved at present in two main ways: in the first method, pins are dipped into the wells to pick up samples of the liquids, and then moved on a three-axis transport to touch the substrates and deposit drops. Several pins may be used in parallel to speed up the spotting.

There are disadvantages to this technology: the pins have to be washed and dried before picking up samples of another set of liquids. The pins have to touch the substrate, which requires high precision, carries a risk of damage, and is slow. The volume of liquid spotted is rather large, is not well controlled and cannot be varied easily. The configuration of spots on the microarray corresponds to the arrangement of liquids in the wells, as the pins are all brought into contact with the substrate simultaneously. A considerable proportion of each liquid is wasted.

The second method of spotting is to project the liquid through the air onto the substrate, without contact. In principle, ink jet printing technology is eminently suitable: it produces small droplets, very reproducibly, and positions them accurately on the substrate. In some cases, the droplets are sufficiently small that multiple droplets can be applied to a given spot to vary its volume. Ink jet printing is very rapid, and is entirely flexible as to what liquid is deposited where on the substrate.

The main difficulty with ink jet technology is that, although some printheads have large numbers of nozzles, they are designed to print typically one or four colours of ink. Their inlets lead to manifolds which connect many chambers, each associated with a nozzle. If such a printhead is applied conventionally to the manufacture of microarrays, the speed of the process is limited by the fact that only one or four liquids is handled at a time, and the fact that there are many nozzles is of little help. The printing itself is very quick, and it is the process of emptying and refilling the printhead which determines the overall manufacturing time.

Other difficulties with ink jet printheads are: some use local boiling of the liquid to eject drops, which could damage some biological samples; others are constructed from materials incompatible with the chemicals to be printed onto microarrays; some are designed for office printers, and are unsuitable for third party integration into industrial systems; and others are designed for industrial use, but require large volumes of liquid to operate.

For the reason given above, standard ink jet printheads are not used in the manufacture of microarrays; rather adapted printheads or devices akin to printheads, are used instead. These do not take advantage of the manufacturing capabilities of ink jet companies, and do not handle large numbers of liquids.

DETAILED DESCRIPTION OF THE INVENTION

The present invention relates to a way of using standard ink jet printheads to handle a number of different liquids larger than the number of colours it is designed to print, without a mixture of the liquids being printed.

In accordance with a first aspect of the present invention there is provided printing apparatus capable of printing a number of different samples without the samples being mixed, wherein the printing apparatus comprises a printhead which itself comprises one or more manifolds, and wherein the number of samples that may be printed is larger than the number of manifolds.

Preferably a manifold is connected to more than one chamber.

Preferably each chamber is associated with one or more nozzle(s).

Preferably there are a number of nozzles which are formed in a nozzle plate.

Most preferably multiple nozzles are used for each sample. This allows multiple drops to be placed on a given spot on a microarray in a single pass. It also extends the useful lifetime of the printhead against the possibility of blockage of nozzles by dirt, or other failure, by ensuring that alternative nozzles are available to print a given sample.

Preferably each chamber is longer in the direction of liquid motion during printing than in a perpendicular direction to the direction of liquid motion during printing.

Most preferably each nozzle is capable of ejecting drops of sample.

Preferably sample liquid is introduced via the nozzles.

Optionally each nozzle acts as a restrictor to control the rate of introduction of liquid into the chamber.

Preferably the printhead is full of fluid at the outset.

Most preferably the fluid is a liquid.

Alternatively the printhead is full of a solid at the outset.

Preferably the solid is a weak solid which has deformable properties.

Preferably, the printing apparatus comprises a connection block attached to the nozzle plate.

Most preferably the connection block comprises seals which act against the printhead nozzles to separate different liquids.

Optionally the connection block may have a layered structure.

Preferably the connection block comprises a filter layer to prevent dirt from entering the printhead.

Optionally the samples are held in wells on a plate (e.g., a microtitre plate) prior to being taken into the printhead.

Preferably the printhead is attached to a moving means which allows the sample to be picked up at one point and expelled at a second point.

Preferably sample is printed over a range of positions.

Alternatively, it is possible that the printhead is stationary and the substrate on which printing is to occur will move relative to the printhead.

Preferably the printhead is positioned so that the line of nozzles is parallel to the direction of motion during printing. Alternatively, the printhead is positioned so that the nozzles run perpendicular to the direction of printing.

Optionally, the printhead is angled in order to alter the effective resolution perpendicular to the motion.

According to a second aspect of the present invention there is provided a method of printing a number of different samples using the apparatus of the first aspect.

Preferably a number of different liquids larger than the number of manifolds is introduced into the chambers via the nozzles.

Preferably, the volume of the liquid printed from each nozzle is less than the volume of the chamber associated with that nozzle, in order to ensure that the liquid printed is uncontaminated by the mixture of liquids likely to be present in the manifolds.

Most preferably the volume of the liquid printed from each nozzle is less than the volume of liquid introduced into the chamber, again in order to avoid contamination.

Preferably the volume of liquid introduced into each nozzle is greater than the volume of the chamber associated with that nozzle, in order to maximise the volume of liquid which can be printed without contamination.

Preferably printing is carried out within a time after the introduction of the different liquids less than the time taken for diffusion to contaminate the liquid in any chamber with liquid from any other chamber via the manifold connecting them.

Preferably the liquids introduced via the nozzles displace the initial liquid towards and into the manifolds.

Optionally, the liquids are introduced into the nozzles by the application of suction to the manifolds. The nozzles act as restrictors to control the rate of introduction of liquid.

Alternatively, the liquids are introduced into the nozzles by the application of pressure in the sample wells so that the liquids are forced in.

Preferably the sample wells are provided with a penetrable seal.

Preferably the wells can each be pressurised separately and different pressures can be applied to each well.

Optionally the wells may be pressurised using pistons.

A further alternative is that the liquids are introduced into the nozzles by the actuation in reverse of the printhead.

Preferably, the volume of each liquid printed is a high proportion of the volume introduced into the printhead.

Preferably the total quantity of liquid printed from each nozzle may be increased above the volume of the associated chamber by:
  a) introducing of a first set of liquids and printing; and
  b) introducing and printing second and subsequent sets of liquids.

Alternatively, if successive sets of liquids are different from earlier sets, this increases the number of different liquids printed, potentially to more than the number of nozzles in the printhead.

Preferably, between the printing of each set of liquids and the introduction of the next set, the printhead is cleaned by the introduction of neutral liquid into the printhead either via the nozzles or via the manifolds.

A commercially promising application of the invention is to print the liquids as spots of picolitre to nanolitre volume onto a substrate for the production of biological or chemical microarrays. An advantage of ink jet printheads is that they can print while there is relative motion between the printhead and the substrate, increasing speed of production.

A specific embodiment of the invention will now be described, purely by way of example, with reference to the accompanying drawings, in which:

FIG. 1 shows a side cross-sectional view of a suitable ink jet printhead;

FIG. 2 shows a front cross-sectional view of a suitable ink jet printhead; and

FIG. 3 shows the liquids being introduced into the printhead from a microtitre plate by means of a connection block.

Referring to FIGS. 1 and 2, each nozzle 1 is associated with a long narrow chamber 4 excavated within lower component 3. The chambers open out at the rear into manifolds 5 each serving multiple chambers. There are typically one or four manifolds 5, each fed by a supply via a filter 6.

Drops are ejected when the walls between the chambers 4 are deflected, causing pressure waves within the chambers 4. The length of the chambers 4, defined by cut-outs in the upper component 2, determines the drop size ejected. If the chambers 4 are long (6 mm in a particular printhead), relatively large drops (typically 50 picolitres) are ejected, which are suitable for binary printing and also for the production of microarrays. If the chambers 4 are short (1 mm in another printhead), small drops (typically 7 picolitres) are produced; then multiple drops can be used for greyscale printing, or for producing microarray spots of controllable size.

In the case of the binary printhead, the chambers 4 are long compared with their lateral dimensions (typically 75 microns by 390 microns), so the liquid tends to advance along the chambers 4 towards the nozzles 1 as printing proceeds; there is little tendency for liquid at the rear of a chamber 4, or that entering the chamber 4 from the manifold 5, to mix with liquid near the nozzle 1. The pathway for diffusion to introduce into a chamber 4 liquid from another chamber 4, via the connecting manifold 5, is long and unfavourable for mixing. Therefore nearly the entire contents of a chamber 4 can be printed without contamination by liquid from elsewhere.

Referring to FIG. 3, a possible embodiment of the invention involves a connection block 10 interposed between the printhead 9 and a microtitre plate 11 to allow multiple liquids to be introduced into the printhead via the nozzles 1. In a preferred embodiment the connection block 10 would include a filter layer.

The connection block 10 has moulded rubber seals 12 which separate multiple regions 13 (typically 48 in number)

of the printhead, each containing several nozzles 1 (typically seven, with three blocked by the seal 12).

Capillaries 14 project downwards from the regions 13 into the wells 15 of a microtitre plate. The pitch of the wells 15 (typically 4.5 mm for a 384-well plate) is larger than that of the regions 13 (typically ten times the pitch 141 microns of the nozzles), so there need to be multiple (typically three) rows of capillaries 14; only one row is shown in FIG. 3.

The printhead 9 may initially be full of a neutral liquid. Suction is applied at point 8 until samples have been drawn into the printhead 9, slightly more than filling the corresponding chambers. The nozzles may act as restrictors to control the flowrate during filling. If the nozzles are of small diameter at their exit faces than internally, they resist ingress of any dirt particles sufficiently large to block nozzles subsequently. The connection block 10 can be equipped with a course filter to minimize the population of dirt particles entering the printhead 9.

An alternative embodiment would have the sample being forced into nozzles 1 from the wells 15. This could be done by pressurising the wells 15, which may be provided with self-sealing covers, so that the liquid is pushed out of them into the nozzles 1; alternatively seals on the lower surface of the connection block could isolate the wells Sealing the wells 15 would have the benefit that different wells 15 could be placed under different pressures so that different amounts of sample could be pushed into the nozzle 1; the seals could also guard against dirt from the atmosphere getting into the printhead. Another way in which samples could be forced into the nozzles 1 is by placing the samples in a pre-loaded cartridge comprising of reservoirs equipped with pistons which push samples out of the reservoirs when required.

As soon as the liquids have been introduced into the printhead 9, it is detached from the connection block 10, wiped and moved by means of an x-y-z motion control to the microarrays to be spotted. The amount of liquid printed from each nozzle 1 is less than the volume of the corresponding chamber 4, so the mixture of liquids in the manifolds 5 is not printed. The timescale of the printing (seconds) does not allow diffusion to contaminate one chamber 4 with the liquid from another. In a preferred embodiment, the row of nozzles 1 is parallel to the direction of relative motion during printing, as this would allow multiple drops to be placed at one point, increasing the amount of liquid at that point.

If the filling and printing are well controlled, the fraction of the liquid drawn from the wells 15 which is wasted should be substantially less than half.

After spotting, the printhead 9 may be taken to a filling station and neutral liquid drawn in through the nozzles. Then another set of liquids can be charged into the printhead 9 and spotted. The use of neutral liquid prevents contamination of the liquid in a chamber 4 by residues of liquids previously introduced into it. Perfect displacement of the liquid in a chamber 4 by neutral liquid entering via its nozzle 1 is impossible, so the volume of neutral liquid introduced into each nozzle 1 should be several times the volume of the chamber 4 associated with that nozzle 1. When the next set of liquids is introduced, they will be diluted slightly by the neutral liquid present in each chamber 4, however, the dilution will be very small and consistent.

At no stage does the printhead 9 have to be dried out, and air never enters w the printhead 9.

Only one nozzle 1 is needed to print the liquid in each region 13. The fact that several nozzles 1 are charged with each liquid means that occasional nozzle blockages or other failures do not limit the lifetime of a printhead 9 in the system. Automated testing of nozzle failures would allow the system to switch to alternative nozzles 1.

The time taken to spot a complex microarray by conventional means is dominated by the speed of the x-y-z motion and the loading of the printhead. Ink jet printers are capable of printing while the printhead is in motion, or the substrate is moving relative to the printhead; and the present invention allows the printhead to be loaded with multiple liquids without emptying and drying the printhead. These advantages lead to a substantial speed improvement relative to mechanical spotting systems.

BRIEF DESCRIPTION OF THE DRAWINGS

To further clarify the above and other advantages and features of the present invention, a more particular description of the invention will be rendered by reference to specific embodiments Thereof which are illustrated in the appended drawings. It is appreciated tat these drawings depict only typical embodiments of the invention and are therefore not to be considered limiting of its scope. The invention will be described and explained with additional specificity and detail through the use of the accompanying drawings in which.

BRIEF SUMMARY OF THE INVENTION

Figure 1:
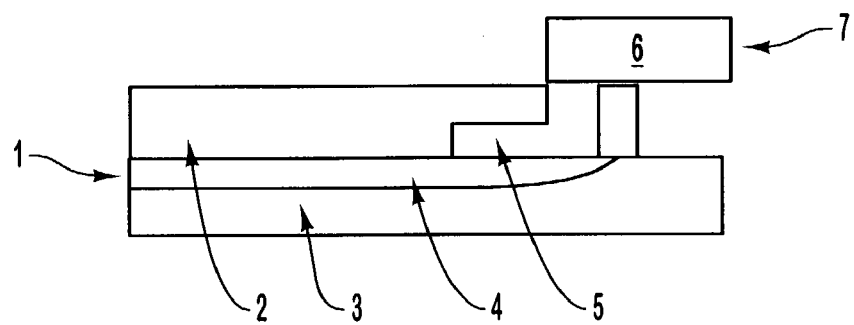
FIG. 1 is a side cross-sectional view of an ink jet printhead in accordance with the present invention.
Figure 2:
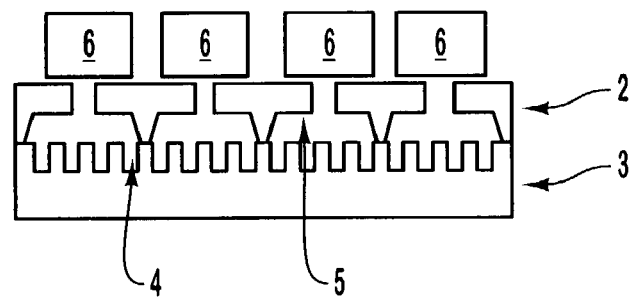
FIG. 2 is a front cross-sectional view of an ink jet printhead in accordance with the present invention.
Figure 3:
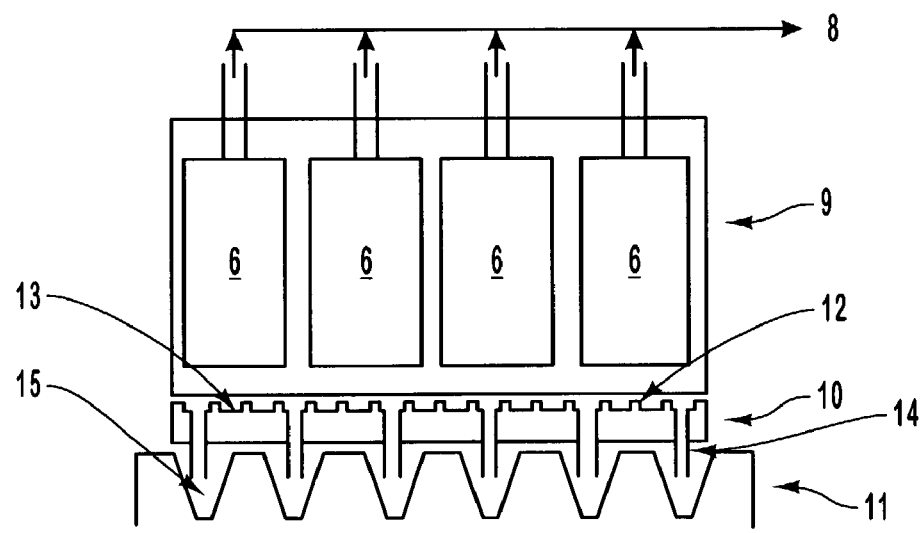
FIG. 3 shows liquids being introduced into a printhead from a microtitre plate by means of connection block.

A method is described of operating an ink jet printhead having one or more manifolds each connected to more than one chamber, each chamber being associated with a nozzle and capable of ejecting drops therefrom: a number of different liquids larger than the number of manifolds is introduced into the printhead via the nozzles; and the volume of the liquid subsequently printed from each nozzle is less than the volume of the chamber associated with that nozzle, and also less than the volume of liquid introduced into that chamber. By this means the printhead prints more different liquids than is conventionally possible without mixing them.

These and other objects and features of the present invention will become more fully apparent from the following description and appended claims, or may be learned by the practice of the invention as set forth hereinafter.

What is claimed is:

1. A printing apparatus comprising:
   a printhead capable of printing a number of different samples without the samples being mixed; and
   at least one manifold associated with the printhead, said at least one manifold being capable of handling a plurality of samples for printing by the printing apparatus, wherein said at least one manifold is provided with a chamber, and wherein a number of different samples larger than the number of manifolds are introduced into chambers via nozzles in the printhead.

2. A printing apparatus as defined in claim 1, wherein the at least one manifold is provided with a plurality of chambers.

3. A printing apparatus as defined in claim 2, further comprising a nozzle associated with each chamber.

4. A printing apparatus as defined in claim 2, wherein the chambers are longer in the direction of liquid motion during printing than in a perpendicular direction to the direction of liquid motion during printing.

5. A printing apparatus as defined in claim 3, wherein each nozzle is capable of ejecting drops of sample.

6. A printing apparatus as defined in claim 1, wherein the printhead is full of fluid at the outset of printing.

7. A printing apparatus as defined in claim 6, wherein the fluid is a liquid.

8. A printing apparatus as defined in claim 1, which can be used to produce microarrays.

9. A printing apparatus comprising:
a printhead capable of printing a number of different samples without the samples being mixed;
at least one manifold associated with the printhead, said at least one manifold being capable of handling a plurality of samples for printing by the printing apparatus; and
a connection block attached to the nozzles.

10. A printing apparatus as defined in claim 9, wherein the connection block is provided with seals which act against the printhead nozzle plate to separate different liquids.

11. A method of printing a number of different samples using a printhead apparatus comprising a printhead capable of printing a number of different samples without the samples being mixed, and at least one manifold associated with the printhead, said at least one manifold being capable of handling a plurality of samples for printing by the printing apparatus, wherein a number of different liquids larger than the number of manifolds are introduced into chambers via nozzles in the printhead.

12. A method of printing a number of different samples, as defined in claim 11, wherein the volume of liquid printed from each nozzle is less than the volume of the chamber associated with that nozzle.

13. A method of printing different samples, as defined in claim 11, wherein the volume of the liquid printed from each nozzle is less than the volume of liquid introduced into the chamber.

14. A method of printing different samples, as defined in claim 11, wherein the volume of liquid introduced into each nozzle is greater than the volume of the chamber associated with that nozzle.

15. A method of printing different samples, as defined in claim 11, wherein printing is carried out within a time after the introduction of different liquids less than the time taken for diffusion to contaminate the liquid in any chamber with liquid from any other chamber via the manifold connecting them.

16. A method of printing different samples, as defined in claims 11, wherein the liquids introduced via the nozzles displace the initial liquid contained in the nozzle towards and into the manifolds.

17. A method of printing different samples, as defined in claim 11, wherein the liquids are introduced into the nozzles via the application of suction to the manifolds.

18. A method of printing different samples, as described in claim 11, wherein the printing apparatus further comprises a connection block, and wherein the liquids are introduced into the nozzles by the application of pressure at the nozzles or to the connection block.

19. A method of printing different samples, as defined in claim 11, wherein liquids are introduced into the nozzles by the actuation in reverse of the printhead.

20. A method of printing different samples, as defined in claim 11, wherein the volume of each liquid printed is a high proportion of the volume that was introduced into the respective chamber.

21. A method of printing different samples as defined in claim 11, wherein the total volume of a given liquid printed can be increased above the volume introduced into the printhead by:
(a) introducing a first set of liquids and printing; and
(b) introducing and printing a second and subsequent set of liquids.

22. A method of printing different samples as defined in claim 21, wherein successive sets of liquids may differ, so that the number of different liquids that may be printed can be increased, potentially above the number of chambers in the printhead.

23. A method of printing different samples, as defined in claim 22, wherein between the printing of a first set of liquids and the introduction of a next set of liquids, the printhead is cleaned by the introduction of a neutral liquid into the printhead.

24. A method of printing different samples, as defined in claim 23 wherein a high proportion of to liquid introduced into the printing apparatus is printed.

25. A method of printing different samples, as described in claim 11, wherein the samples are able to be printed while the printhead is moving.

26. A method of printing different samples as defined in claim 11 which can be used to produce microarrays.

* * * * *

UNITED STATES PATENT AND TRADEMARK OFFICE
CERTIFICATE OF CORRECTION

| | | |
|---|---|---|
| PATENT NO. | : 7,128,393 B2 | Page 1 of 1 |
| APPLICATION NO. | : 10/350776 | |
| DATED | : October 31, 2006 | |
| INVENTOR(S) | : Manning | |

It is certified that error appears in the above-identified patent and that said Letters Patent is hereby corrected as shown below:

Column 1
Line 14, change "filed" to --field relates--

Column 5
Line 63, remove "w"

Column 6
Line 18, change "Thereof" to --thereof--
Line 19, change "tat" to --that--

Column 8
Line 39, change "to" to --the--

Signed and Sealed this

Twenty-second Day of May, 2007

JON W. DUDAS
*Director of the United States Patent and Trademark Office*